US011072769B2

(12) United States Patent
Czwaluk

(10) Patent No.: US 11,072,769 B2
(45) Date of Patent: Jul. 27, 2021

(54) AGITATING DEVICE FOR A DIGESTER OF A BIOGAS PLANT AND METHOD FOR MANUFACTURING AN AGITATING DEVICE

(71) Applicant: UTS BIOGASTECHNIK GMBH, Hallbergmoos (DE)

(72) Inventor: Andreas Czwaluk, Vechta (DE)

(73) Assignee: UTS BIOGASTECHNIK GMBH, Hallbergmoos (DE)

(*) Notice: Subject to any disclaimer, the term of this patent is extended or adjusted under 35 U.S.C. 154(b) by 555 days.

(21) Appl. No.: 15/035,133

(22) PCT Filed: Nov. 7, 2014

(86) PCT No.: PCT/EP2014/074025
§ 371 (c)(1),
(2) Date: May 6, 2016

(87) PCT Pub. No.: WO2015/067745
PCT Pub. Date: May 14, 2015

(65) Prior Publication Data
US 2016/0289622 A1    Oct. 6, 2016

(30) Foreign Application Priority Data
Nov. 8, 2013    (DE) .................... 10 2013 018 690.0

(51) Int. Cl.
*C12M 1/107*    (2006.01)
*B01F 15/00*    (2006.01)
(Continued)

(52) U.S. Cl.
CPC ............. *C12M 21/04* (2013.01); *B01F 7/001* (2013.01); *B01F 7/00341* (2013.01);
(Continued)

(58) Field of Classification Search
CPC ...... C12M 21/04; C12M 23/00; C12M 23/38; C12M 27/02; B01F 7/001; B01F 7/00341;
(Continued)

(56) References Cited

U.S. PATENT DOCUMENTS 2,794,628 A    6/1957    Fessenden
4,147,437 A    4/1979    Jonqueres
(Continued)

FOREIGN PATENT DOCUMENTS

DE    2624991 A1    12/1976
EP    0469302 A1    2/1992
(Continued)

OTHER PUBLICATIONS

English Translation of KR 100970137 accessed Jan. 2019 (Year: 2019).*
(Continued)

*Primary Examiner* — William H. Beisner
*Assistant Examiner* — Danielle B Henkel
(74) *Attorney, Agent, or Firm* — Greer, Burns & Crain, Ltd.

(57) ABSTRACT

Digester (1) having an agitating device (10) and an agitating device (10) and a method for manufacturing an agitating device (10), the agitating device (10) comprising multiple agitator blades (21-29) which agitator blades (11-13) comprise a plurality of blade sections (21-29) angled relative to one another. The blade sections (21-29) of the agitator blade (11-13) are angled relative to one another such that the agitator blade gradient (11-13) decreases with the distance (30) from a central rotational axis (19) increasing to configure the agitator blade in a flow-optimized three-dimensional shape.

22 Claims, 3 Drawing Sheets

(51) Int. Cl.
  *C12M 1/06* (2006.01)
  *B01F 7/00* (2006.01)
  *B01F 7/06* (2006.01)
  *C12M 1/00* (2006.01)

(52) U.S. Cl.
  CPC ............ *B01F 7/00733* (2013.01); *B01F 7/06* (2013.01); *B01F 15/00922* (2013.01); *C12M 23/00* (2013.01); *C12M 23/38* (2013.01); *C12M 27/02* (2013.01); *B01F 2215/0073* (2013.01); *Y02E 50/30* (2013.01)

(58) Field of Classification Search
  CPC .. B01F 7/00733; B01F 7/06; B01F 15/00922; B01F 2215/0073; Y02E 50/343
  See application file for complete search history.

(56) References Cited

U.S. PATENT DOCUMENTS

| | | | |
|---|---|---|---|
| 4,479,721 | A | 10/1984 | Rieger |
| 6,334,705 | B1 | 1/2002 | Weetman |
| 7,473,025 | B1 | 1/2009 | Howk |
| 10,105,663 | B2 * | 10/2018 | Cognart .............. B01F 7/00375 |
| 2006/0092762 | A1 | 5/2006 | Casalmir et al. |
| 2012/0009664 | A1 * | 1/2012 | Buerger ................. C12M 21/04 435/286.5 |
| 2012/0039721 | A1 | 2/2012 | Lilja et al. |
| 2015/0240832 | A1 * | 8/2015 | Xia .................... B01F 7/00375 416/243 |
| 2017/0306983 | A1 * | 10/2017 | Strommer ............. F04D 29/648 |
| 2020/0040906 | A1 * | 2/2020 | Yamamoto ............ F04D 29/384 |

FOREIGN PATENT DOCUMENTS

| | | |
|---|---|---|
| EP | 0711586 A2 | 5/1996 |
| EP | 1876229 A1 | 1/2008 |
| KR | 100970137 B1 | 7/2010 |

OTHER PUBLICATIONS

Office Action issued in related German Patent Application Application Serial No. 10 2013 018 690.0 dated Jul. 29, 2014.
International Search Report and Written Opinion issued in related International Patent Application No. PCT/EP2014/074025 dated Feb. 19, 2015.
Canadian Patent Application No. 2,929,904, Office Action dated Jun. 22, 2017.
Canadian Patent Application No. 2,929,904, Office Action dated Jan. 11, 2018.
Canadian Patent Application No. 2,929,904, Office Action dated Aug. 17, 2018.
European Patent Application No. 14802828.5, Office Action dated Mar. 22, 2017—English Translation Available.
European Patent Application No. 14802828.5, Summons to Attend Oral Proceedings dated May 3, 2019—English Translation Available.
LJM Industrie., "Effektive Abwasserbehandlung," 2012, 11 pages— English Translation Not Available. (Note: this is reference D11 in the "European Patent Application No. 14802828.5, Summons to Attend Oral Proceedings dated May 3, 2019" mentioned above).
LJM Industrie., "Waste Water Handling," 19 pages. (Note: this is reference D12a-d in the "European Patent Application No. 14802828.5, Summons to Attend Oral Proceedings dated May 3, 2019" mentioned above).
Stallkamp.,"Betriebsanleitung—Tauchmotorruhrwerk Typ 3 Modell 2008 GL," May 2010, 43 pages—English Translation Not Available. (Note: this is reference D13a-d in the "European Patent Application No. 14802828.5, Summons to Attend Oral Proceedings dated May 3, 2019" mentioned above).
Stallkamp.,"Betriebsanleitung—Tauchmotorruhrwerk Typ 3 Modell 2008," Jan. 2010, 35 pages—English Translation Not Available. (Note: this is reference D14a-b in the "European Patent Application No. 14802828.5, Summons to Attend Oral Proceedings dated May 3, 2019" mentioned above).

* cited by examiner

AGITATING DEVICE FOR A DIGESTER OF A BIOGAS PLANT AND METHOD FOR MANUFACTURING AN AGITATING DEVICE

CROSS-REFERENCE TO RELATED APPLICATIONS

This application is a National Stage Entry of International Application No. PCT/EP2014/074025, filed Nov. 7, 2014, which claims the benefit of German Application Serial No. DE 10 2013 018 690.0, filed Nov. 8, 2013.

BACKGROUND

The present invention relates to an agitating device in particular for a digester of a biogas plant, a digester equipped with such an agitating device, and such a biogas plant and a method for manufacturing an agitating device.

Biogas plants comprise as a rule a digester or several digesters into which a substrate is introduced to generate biogas. It is necessary to stir or agitate the substrate in the digester interior to obtain and ensure favorable conditions for operating the digester.

Stirring is done by means of agitators or agitating devices which as a rule comprise one or more agitator blades to agitate the substrate. The agitator blades are subjected to heavy wear since the substrates used in the digesters may be very abrasive. Therefore the agitator blades require regular replacement. Agitators having agitator blades of sheet metal have therefore been disclosed wherein the metal sheet is edge-bent for manufacturing the agitator blades. This provides for ease of manufacturing and for low costs for the agitator blades.

KR 100970137 B1 has disclosed an agitator having agitator blades wherein each blade is edge-bent three-fold. The agitator serves for water treatment and is intended to prevent bottom sediments in the center. To this end, blade vibration in operation is reduced by way of bending the radially outwardly end of the agitator blades parallel to the axis.

US 2012/0039721 A1 shows an agitator for hydrometallurgy processes having five agitator blades simple in design whose structure is obtained by edge-bending the flat sheet profiles twice. The advantage of this is the comparatively low manufacturing costs. The agitator is therefore suitable for use in hydrometallurgy processes.

In biogas plants, however, the digester must quite frequently and predominantly continuously agitate highly viscous mixtures to prevent the formation of floating sludge layers and the deposit of certain solid substances in the digester and to sweep out gas bubbles upwardly. Continuous agitating operation is the rule in abrasive medium. Agitating these media is highly energy-consuming. The electric power required for an agitator is as a rule 16 kW to 17 kW so that high energy costs arise in permanent agitating operation. Therefore the energy consumption in operation is as significant as are the manufacturing costs. Although agitators having edge-bent agitator blades involve low manufacturing costs, their flow properties are less than optimal, thus generating high operating costs since their efficiency is low.

Efficient agitators comprise propeller-type agitator blades having a flow-optimized three-dimensional shape. While agitator blades in these shapes and three-dimensional configurations are more cost-effective in operation due to reduced energy consumption, these agitator blades are expensive in manufacturing. Mass production for keeping the costs down is not readily feasible since the quantities of agitator blades required are too small.

SUMMARY

It is therefore the object of the present invention to provide an agitating device and a digester equipped with such an agitating device, and a method for manufacturing an agitating device so as to enable more economical production of biogas.

An agitating device according to the invention is in particular provided to be employed in a digester of a biogas plant and comprises at least one agitator blade. The agitator blade comprises a plurality of blade sections angled to one another for a flow-optimized three-dimensional configuration of the agitator blade. The blade sections are in particular angled relative to one another such that with the distance from a central rotational axis increasing, the agitator blade gradient decreases for a flow-optimized three-dimensional configuration of the agitator blade.

The agitating device according to the invention has many advantages. A considerable advantage of the agitating device according to the invention is the simple structure so as to allow easy manufacturing while concurrently allowing low energy operation. The fact that the agitator blade comprises a plurality of blade sections each being angled relative to one another allows to obtain a flow-optimized shape of the agitator blade. The shape of the agitator blade and the inclination of the blade and the diameter can be oriented at the mounting space and the desired direction of flow.

The invention provides an agitating device that can be readily manufactured manually or machine-aided or even fully automatically, from simple components. The cost-effectiveness achieved is particularly considerable in small and extra small series while concurrently allowing a flow-optimized shape.

The flow-optimized shape allows to realize energy savings of 25% and more and in particular even 33%, 40% and preferably 50% and more. It is possible to reduce the overall power requirement from 16 kW or 17 kW to 12 kW and in particular to less than 10 kW. The shape of the agitator blade prevents single sections of the effective cross-sectional area from counteracting one another. It is possible to provide for little variations in the advancing drive over the entire cross-sectional area. In conventional mixers or agitators with radially extending bent edges the advancing drive increases with increasing distance so that considerable friction loss occurs over the entire cross-sectional area.

Another agitating device according to the invention is in particular provided for a digester of a biogas plant, comprising at least one blade hub rotatable about a rotational axis and a plurality of agitator blades attached thereto. Each agitator blade comprises a blade body and a blade base in particular immediately on, or adjacent to, the blade hub. A radially inwardly blade surface and/or the blade surface at the blade base extends at an angle between 15° and 75° to the rotational axis of the blade hub. The blade body consists entirely or substantially of a plurality of blade sections angled relative to one another. The blade sections are angled relative to one another such that the agitator blade gradient decreases with the distance from a central rotational axis increasing so as to configure the agitator blade in a flow-optimized three-dimensional shape.

In all the specific embodiments and configurations the blade sections of an agitator blade are preferably integrally connected with one another on the whole.

It is particularly preferred for the blade sections of an agitator blade to be formed by bending over a flat basic body multiple times. The basic body may for example consist of a metallic material and in particular of sheet metal. It is for example possible to form the blade sections of an agitator blade and virtually the entire agitator blade from an originally flat steel plate which is bent over or edge-bent at the edges of the respective blade sections.

It is particularly preferred for the blade sections to be substantially configured flat. This means that in particular substantially each blade section and preferably each blade section shows a flat structure.

In particular at least part of the plurality of the blade sections is substantially flat in structure. In particular substantially all the blade sections and in particular all the blade sections are flat in structure. A flat structure in the sense of the present invention is understood to mean a structure showing only insubstantial elevations over its surface. The elevations of a flat structure are preferably less than four times the material thickness. The elevations of the structure may be less than twice the material thickness.

The structure of at least part of the blade sections is in particular substantially square. The blade sections are in particular configured in stripes. Or else triangular blade sections and also rectangular blade sections are possible. Blade sections tapering to one end allow to obtain a suitable three-dimensional structure overall so rectangular blade sections tend to be employed but rarely.

In preferred embodiments at least one of the blade sections shows an elevation transverse to its blade surface that is less than four times the material thickness of the blade section. This applies in particular to each of the plurality of blade sections.

Preferably the agitator blades are three-dimensional in shape. The agitator blades extend both in the axial direction of the rotational axis and also in the radial direction. An agitator blade mounted to the blade hub preferably extends in the axial direction (axial extension) over at least ⅙ of a maximum radial extension of the agitator blade starting from the rotational axis. The axial extension is in particular at least ⅕ of a radial extension of the blade body.

In all the configurations it is preferred for a bending edge to substantially extend linearly so as to define, and/or to be disposed between, pairs of adjacent blade sections.

At least one bending edge or all or some of the bending edges show in their orientation, other than a radial component transverse to a rotational axis, also an axial component parallel to the rotational axis of the blade hub, wherein with the radial distance of a bending edge from the rotational axis increasing, the axial component of the bending edge decreases.

In all the configurations it is preferred to provide the agitator blade with at least 4, 5, 6, 7, 8 or more blade sections. It is also possible to provide 10, 12, 14 or still more blade sections. With the quantity of the blade sections increasing, the adaptability of the three-dimensional structure increases as well wherein a higher number of blade sections allows better conformity with the theoretically ideal geometry of the agitator blade. On the other hand the manufacturing complexity also increases with the number of blade sections so that a number between 4 and 20 blade sections and in particular between 6 and 15 blade sections has been found favorable. The quantity and type of blade sections also depends on the intended application and on the material thickness and the type of material of the agitator blade.

Preferably at least one angle between pairs of adjacent bending edges is larger than 1°. Preferably all the angles between pairs of adjacent bending edges are larger than 0.5° and in particular larger than 1°. Adjacent bending edges preferably extend fan-like away from one another.

In all the configurations it is possible and preferred to provide at least one blade section to be edge-bent.

Preferably the agitator blade gradient decreases with the distance from a central rotational axis of the agitating device increasing.

In the case of agitating devices for digesters for biogas plants it is advantageous to have an approximately uniform advancing drive over the entire diameter of the agitating device respectively of the propeller. Thus it follows that the local angles of the agitator blades respectively the angles of the blade positions relative to the central rotational axis are dependent on the respective diameter. This means that the angle of the agitator blade relative to the central axis or the rotational axis is steeper close to the center than it is radially further outwardly. It is therefore preferred that the product of the distance from the central rotational axis and the local agitator blade gradient varies over the blade surface by less than the value of 10 and in particular less than the value of 4 and preferably less than the value 2 or even 1.5. This provides for a relatively uniform advancing drive over the entire diameter of the agitating device.

Preferably a local inclination angle in a surface location of the agitator blade relative to an axis extending through the surface location and oriented transverse to the central rotational axis is dependent on the distance from the central rotational axis. The local inclination angle preferably decreases as its distance from the central rotational axis increases.

In preferred specific embodiments the agitator blade is attached to a mounting device. The mounting device may basically be configured as desired and in a concrete embodiment it is configured as an angled mounting plate. This again achieves easier manufacturing.

In all the configurations it is particularly preferred to provide a plurality of at least two or three or more agitator blades. They are disposed in particular symmetrically over the circumference.

It is particularly preferred for the mounting devices of the agitator blades to overall form a multi-edged axle mount. For example the mounting devices of three agitator blades together may form a hexagonal outer surface, each of the agitator blades being attached to two outer edges by means of an angled mounting plate.

Particularly preferably the agitator blade is attached to the mounting device or to a separate axle mount via at least one detachable connecting device. Such a detachable connecting device may for example be a screw.

In preferred embodiments the agitating device comprises a driving device and at least one drive shaft. The agitator blade may be at least substantially non-rotatably connected with a drive shaft. For reasons of manufacture or for other reasons the agitator blade may show a certain rotary play. The driving device may basically be configured as desired. Electrical driving devices and also hydraulic driving devices are possible and preferred.

A digester according to the invention in particular for a biogas plant comprises at least one digester wall and at least one digester interior. At least one digester roof is provided. The digester wall and the digester roof may consist of a great variety of materials. Digesters of concrete or similar materials are possible. Digesters of steel are likewise possible. The digester roof may be configured as a solid roof or else provided as a flexible film roof. In the digester interior at least one agitating device is disposed which agitating device comprises at least one agitator blade. The agitator blade comprises a plurality of blade sections angled to one another for a flow-optimized three-dimensional configuration of the agitator blade. The agitating device of the digester according to the invention is configured as is an agitating device according to the invention as described above or any of the specific embodiments.

The digester according to the invention also has many advantages. This digester allows reliable operation requiring little energy providing for cost effective acquisition of agitator blades which are wearing parts. The agitator blades are furthermore preferably attached separately and thus they can even be replaced singly.

A method according to the invention serves to manufacture an agitating device in particular for a digester of a biogas plant, the agitating device comprising at least a plurality of agitator blades. An agitator blade is formed of a plurality of blade sections angled relative to one another. The blade sections of the agitator blades are bent over at such an angle relative to one another that the agitator blade gradient decreases with the distance from a central rotational axis increasing so as to configure the agitator blade in a flow-optimized three-dimensional shape. The method according to the invention has many advantages since it allows easy and more cost effective manufacture of an agitator blade which furthermore enables an energetically efficient operation. This agitator blade allows cost effective manufacture even in small and extra small series. Depending on the size of the series, manual manufacture or partially or fully automated manufacture is feasible.

The agitator blade is preferably manufactured from a two-dimensional basic body by bending over each of the blade sections. The initially two-dimensional basic body such as a flat-lying steel plate is first cut in the desired developed view and then the single blade sections are formed from the basic body by bending over.

Advantageously the flat basic body is bent and in particular edge-bent on a separation line between the blade sections. A number of successive bending or edge-bending processes to the respective blade sections allows to achieve a good approximation of the desired three-dimensional shape. The product fulfills the desired requirements for the volume flow, the flow direction, and energy demand.

In all the configurations it is preferred for at least several agitator blades to be directly or indirectly connected with one another by detachable connecting devices. The agitator blades may be attached to mounting devices in the shape of for example angled mounting plates which mounting devices are in turn directly or indirectly connected with one another.

The structure of the agitator blade is such that the angle between two blade sections depends on the distance from the rotational axis.

In all the configurations the diameter of the one agitator blade or the plurality of agitator blades is selected in coordination with the mounting space. The blade inclination of the agitator blade is selected by the desired flow direction. The gradient may be selected by the relationship between the pushing force and the energy employed or else by the volume flow in relation to the energy employed. The gradient, i.e. the advancing drive, is preferably selected such that the drive is approximately uniform over the entire diameter of the agitating device. This results in an angle of the blade positioning of the agitator blade relative to the rotary shaft which varies depending on the local diameter, the angle being steeper near the hub and flatter at the outer diameter.

The relative rolling curve for manufacturing the basic body is selected such in the rotational direction that rolling off works without ragging. The result is a freeform surface in 3D which can be well approximated in bending processes.

The plates for the basic body and other parts are cut so as to provide for low-equipment joining. Contours and engravings can be made so as to apply on the basic body the edge lines, the provided steps and the bending angles intended so that the subsequent manufacturing steps are clearly recognizable.

A device is possible for finishing where the single components can be clearly positioned to thus allow visual inspection of the geometry.

Further advantages and applications of the present invention can be taken from the exemplary embodiment which will be described below with reference to the enclosed figures.

DETAILED DESCRIPTION

Figure 1:
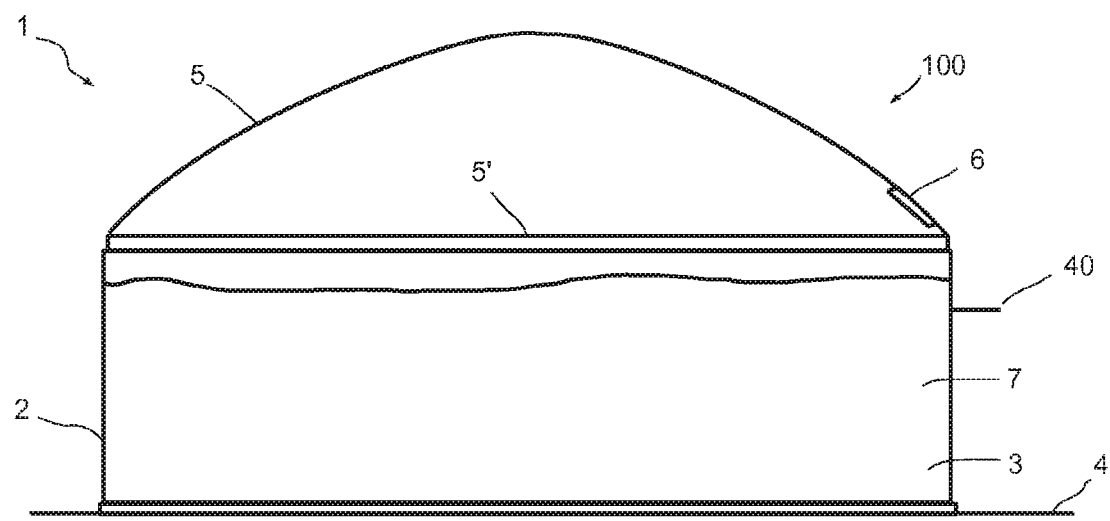
FIG. 1 a schematic side view of a digester according to the invention.

Referring to the figures an exemplary embodiment will now be explained. FIG. 1 shows a simplistic side view of a digester 1 of a biogas plant 100. The digester 1 is preferably approximately circular in cross section and is presently provided with a circumferential digester wall 2 for example of concrete or steel. The digester roof 5 may be configured as a flat steel or concrete roof 5', as may the floor. This digester roof 5 is formed by an in particular flexible material, extending upwardly from the wall so that a domed structure of the tank roof 5 is obtained. The inclination angle of the digester roof 5 depends on the specific conditions and may be 15° or more and in particular 30° or 45° or more. Preferably the digester roof 5 is at least partially and in particular entirely removable to render the digester interior 3 accessible.

In the digester interior 3 a substrate 7 is provided when in operation.

The digester roof 5 may be provided with at least one servicing opening 6 for example for servicing an agitator 10 disposed in the digester interior 3. A platform may be attached for example to the outside of the digester wall 2 for an operator to stand on.

Figure 2:
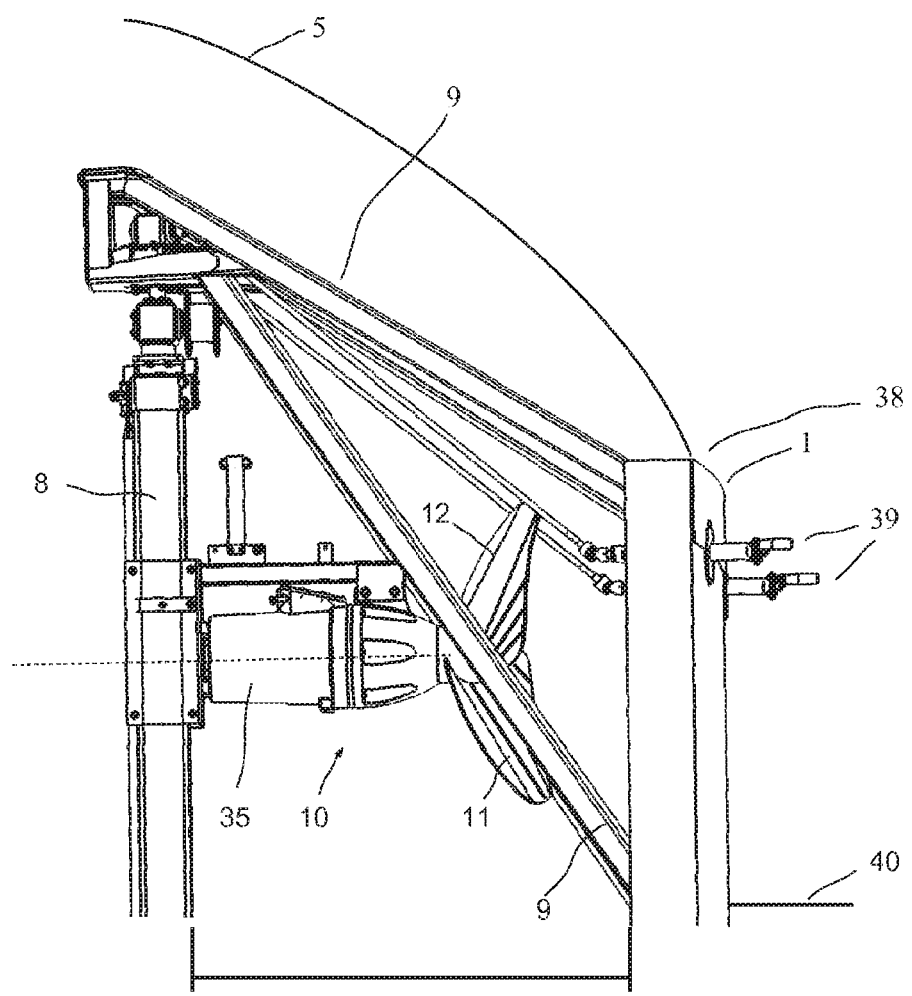
FIG. 2 a schematic cross section of the top end of the digester wall and an agitating unit according to the invention pulled relatively far upwardly.

FIG. 2 shows a partial cross-section of the digester wall 2 where the agitating device 10 is visible with two of the agitator blades 11-13 provided thereat.

The agitating device 10 is configured as a submersible motor agitator and it may be driven electrically or for example also hydraulically. In this exemplary embodiment the schematically illustrated agitator 10 is provided with a plurality of e.g. three agitator blades 11-13 which rotate when the agitating device is in operation, thus obtaining a thorough mixing of the substrate 7 in the digester interior 3. This allows homogenization and enhanced efficiency.

The agitator 10 is retained height-adjustable at a guide unit 8 configured as a support mast or hollow profile.

The agitator 10 may be traversed from the position illustrated in FIG. 2 far enough upwardly so that it abuts against the top edge of the guide unit 8. The agitating device 10 can be lowered along the guide unit 8 until the agitator blades 11 to 13 are just a short distance above the digester floor.

The agitator 10 is provided pivotable together with the approximately rectangular support mast respectively with the guide unit 8 which is approximately rectangular in cross-section or has some other shape. The guide unit 8 can rotate about its longitudinal axis for pivoting the agitator 10 and for adjusting the agitating angle. This allows to align the agitator 10 in any desired direction.

The guide unit 8 is attached to the inside surface of the digester wall 2 and retained thereat via support units 9. The support units 9 each comprise one or more supporting rods which extend upwardly at an angle. This allows to effectively support the guide unit 8.

The fact that when in the servicing position the agitator blades 11 to 13 extend at least in part beyond the top end 38 of the digester wall 2 allows a maintenance technician standing on the platform 40 to comparatively comfortably exchange one or more of the agitator blades 11 to 13.

Adjusting units 39 are provided for adjusting the height of the agitator 10 and for adjusting the pivoting angle of the agitator 10.

As is schematically illustrated in FIG. 2, the agitator blades 11, 12 each comprise a plurality of blade sections. The structure of the agitator blades 11 to 13 and their architecture will now be described in detail with reference to the FIGS. 3 and 4.

Figure 3:
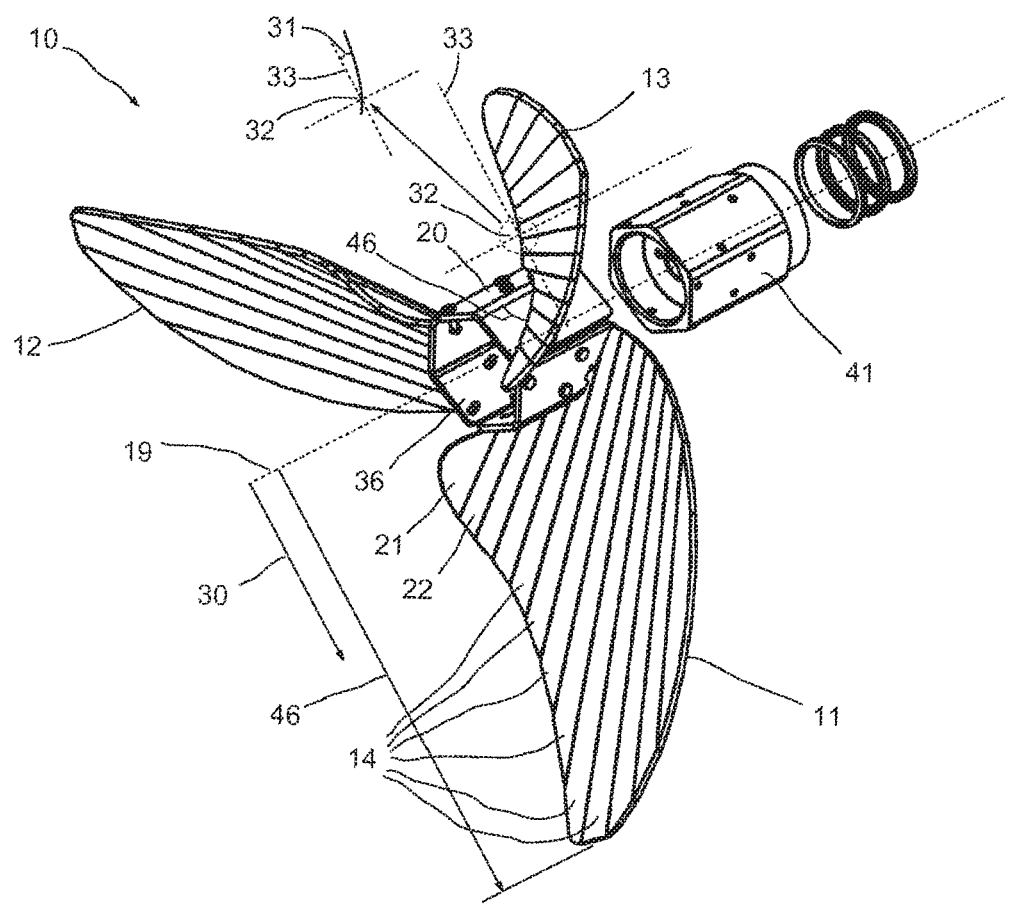
FIG. 3 a perspective illustration of an agitating device according to the invention.

FIG. 3 shows a perspective illustration of the agitating device 10 which is presently equipped with three agitator blades 11, 12 and 13.

Each of the agitator blades 11 to 13 is attached to a mounting device 20. The entire mounting device 20 of the three agitator blades 11 to 13 provides an axle mount 36 which serves to receive the drive shaft of the agitator. The drive shaft is fastened in the hub 41 which is pushed into, and screwed with, the axle mount 36. Thus each of the three agitator blades 11, 12, 13 is exchangeable separately. For exchanging, the screws provided as connecting devices 34 for the respective agitator blade 11 to 13 are unscrewed so that the agitator blade can be removed and exchanged.

Each of the agitator blades 11 to 13 comprises a plurality 14 of blade sections 21, 22, etc. consisting of planes and flat segments.

The agitating device 10 is rotatable about the central rotational axis 19. The agitator blade gradient decreases with the distance 30 from the central rotational axis 19 increasing. This allows a substantially uniform drive over the cross-sectional area of the agitating device 10.

To this end the inclination angle 31 in a surface location 32 is dependent on the distance 30 from the central rotational axis relative to an axis 33 extending through the surface location 32 that is aligned transverse to the central rotational axis 19. Thus: the longer the distance 30, the smaller the inclination angle 31.

The agitator blades of the agitating device 10 are attached to a blade hub 41 rotatable about a rotational axis 19. The or each of the agitator blades 11-13 comprises a blade body 43 and a blade base 44 adjacent to the blade hub 41. These blade bodies 43 extend immediately up to the blade hub 41. The radially inwardly blade surface 45 extends at an angle 46 between 15° and 75° and in particular between approximately 25° and 60° to the rotational axis 19 of the blade hub 41.

At least one of the agitator blades and in particular all of the agitator blades 11-13 mounted to the blade hub 41 extend in the axial direction of the rotational axis 19 over at least 1/6 and in particular more than 1/5 of a maximum radial extension 46 of the agitator blade from the rotational axis 19.

This means that on the blade base the agitator blades extend inclined relative to the blade hub 41. The blade sections of the agitator blades 11-13 are angled relative to one another such that the agitator blade gradient 11-13 decreases with the distance 30 from a central rotational axis 19 increasing so as to configure the agitator blades 11-13 in a flow-optimized three-dimensional shape.

Figure 4:
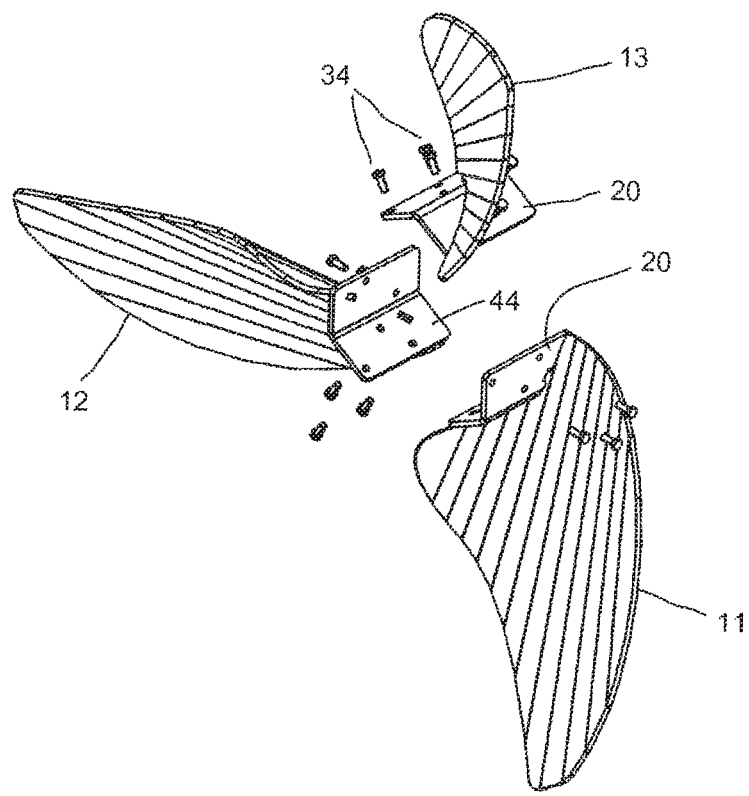
FIG. 4 a perspective exploded illustration of an agitating device according to the invention.

FIG. 4 shows an exploded perspective view of the agitating device 10 with the three agitator blades 11, 12 and 13. Each of the agitator blades 11 to 13 in this exemplary embodiment is welded to its mounting device 20. Other attachment options are possible and conceivable. The mounting devices 20 in turn are screwed to the hub 41 through the connecting devices 34 which in this case are screws.

Figure 5:
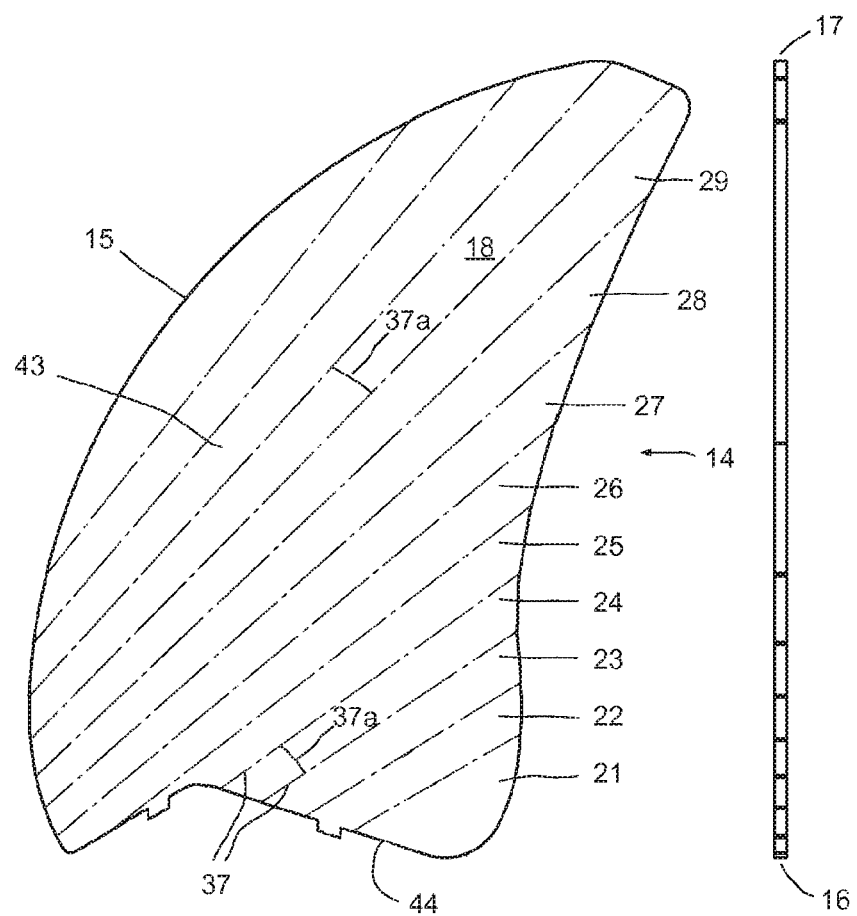
FIG. 5 the basic body of an agitator blade of the agitating device according to the invention in a top view and side view.

FIG. 5 shows the basic body 15 for an agitator blade 11 to 13 before the agitator blade is given its final shape. The agitator blades 11 to 13 are each manufactured from a flat steel plate or the like, firstly showing a flat and plane structure with a consistent wall thickness over the surface. The developed view of the agitator blade 11 to 13 is cut from a flat-lying steel plate so as to obtain a basic body 15 as it is shown in the left half of FIG. 5 in a top view.

The basic body 15 can for example be cut out by means of lasering. Additional markings and indicators can be applied onto the blade surface 18 of the agitator blade by means of lasering or other devices. The individual blade sections 21 to 29 etc. are for example delineated on the basic body 15. Thus the bending lines are already applied onto the blade surface as the basic body 15 is cut. Indicators for the bending angles and the sequence of the process steps may for example be written thereon so that in manual processing, information about the type and sequence of the next process steps is available to the operator at all times.

Figure 6:
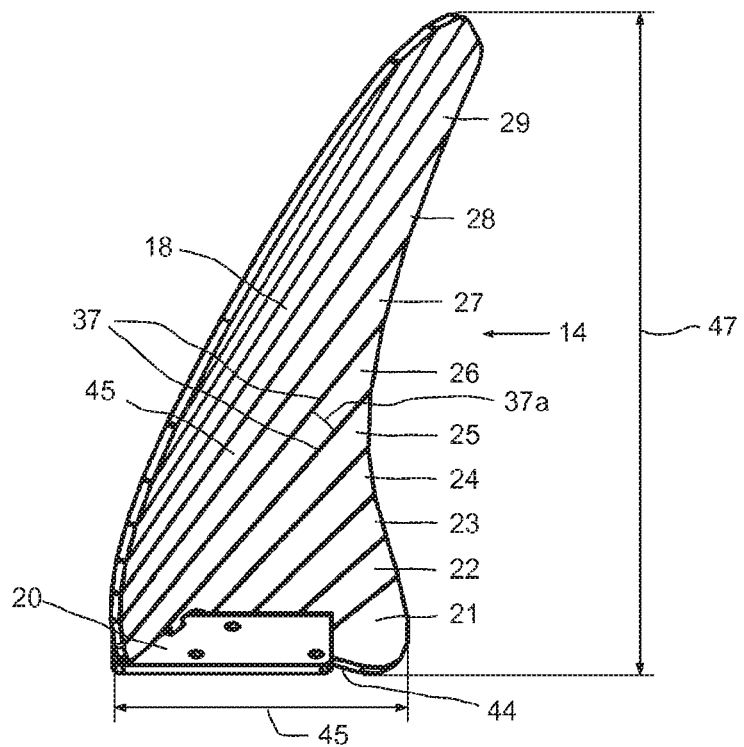
FIG. 6 the agitator blade generated from the basic body of FIG. 5.

The number of blade sections 21 etc. depends on the application and requirements. The illustrated agitator blade shows a total of about 13 different blade sections wherein only the blade sections 21 to 29 are denoted with reference numerals. Each of the blade sections is configured as a stripe with the separation lines 37 between blade sections extending linearly although they may show angles 37a relative to one another. This enables a simple bending process for manufacturing the finished agitator blade. The separation line 37 concerned must be suitably placed or disposed on the bending machine or edging machine prior to bending the intended angle. After carrying out the plurality of bending actions the structure illustrated in FIG. 6 is obtained where the agitator blade extends to the front out of the plane of the drawing. Each of the blade sections 21 etc. then shows a substantially plane blade surface 18. A three-dimensional and flow-optimized structure is obtained by the plurality of the bent-over blade sections. In this way an ideal agitator blade contour is closely approximated. At the same time this manufacturing type allows cost-effective manufacturing of the agitator blades which due to the limited field of applications are produced in small or very small series and as a rule at least partially manually.

The individual blade sections 21-29 show between them separation lines or bending edges 37 along which the blade sections 21-29 are bent over and/or edge-bent. In the finished agitator blades the separation lines 37 are bending edges 37 which extend substantially or entirely linearly between pairs of adjacent blade sections.

The bending edges 37 show in their orientation, other than a radial component transverse to the rotational axis 19, also an axial component parallel to the rotational axis 19. With the radial distance of a bending edge 37 from the rotational axis 19 increasing, the axial component of the path of the bending edge 37 decreases.

An angle between pairs of adjacent bending edges 37, e.g. the blade sections 26, 27 and 27, 28, is preferably larger than 1°. In particular all the angles between pairs of adjacent bending edges are larger than 0.5° and in particular larger than 1°. Preferred angles range between 0.5° and 3°. As illustrated in FIG. 5, adjacent bending edges preferably extend fan-like away from one another.

As can be taken from the right-hand part of FIG. 5 showing a side view of the basic body 15, the basic body has a material thickness 16 of an elevation 17 which is maintained in virtually each of the blade sections 21 etc. Only the edges and bending edges of the blade sections may show a slightly larger elevation due to bending. The elevation 17 of a blade section therefore virtually always remains less than double the material thickness 16. Optionally with the exception of the bending locations.

When creating the 3D contour and the developed view as it is illustrated in FIG. 5, care is taken to enable a suitable bending sequence.

On the whole an agitating device or an agitator 10 is obtained and a digester equipped therewith, which show considerably reduced energy consumption since the three-dimensional contours of the agitator blades can be optimally adapted to the theoretically optimal contour. A quantity of only 4 and better 6 or 8 bends provide an effective agitating device the manufacture of which is still cost effective. Each of the agitator blades 11 to 13 of the agitating device can be exchanged separately.

Although each of the blade sections 21 etc. consists of a plane metal strip having a material thickness 16, a flow-optimized and effective agitating device is provided on the whole.

While a particular embodiment of the present stirrer unit for an agitating device for a digester of a biogas plant and method for manufacturing an agitating device has been described herein, it will be appreciated by those skilled in the art that changes and modifications may be made thereto without departing from the invention in its broader aspects and as set forth in the following claims.

When the manufacturing process and each of the bending steps provide for employing suitable templates and brackets, manual manufacture also enables efficiency of process.

List of reference numerals:

| | |
|---|---|
| 1 | digester |
| 2 | digester wall |
| 3 | digester interior |
| 4 | horizontal |
| 5 | digester roof |
| 6 | servicing opening |
| 7 | substrate |
| 8 | guide unit |
| 9 | support unit |
| 10 | agitator, agitating device |
| 11 | agitator blade |
| 12 | agitator blade |
| 13 | agitator blade |
| 14 | plurality |
| 15 | main body |
| 16 | material thickness |
| 17 | elevation |
| 18 | blade surface |
| 19 | rotational axis |
| 20 | mounting device |
| 21 | blade section |
| 22 | blade section |
| 23 | blade section |
| 24 | blade section |
| 25 | blade section |
| 26 | blade section |
| 27 | blade section |
| 28 | blade section |
| 29 | blade section |
| 30 | distance |
| 31 | inclination angle |
| 32 | surface location |
| 33 | axis |
| 34 | connecting device |
| 35 | driving device |
| 36 | axle mount |
| 37 | separation line, bending line |
| 37a | angle |
| 38 | end |
| 39 | adjusting unit |
| 40 | platform |
| 41 | hub, blade hub |
| 43 | blade body |
| 44 | blade base |
| 45 | axial extension |
| 46 | radial extension |
| 47 | radial length |
| 100 | biogas plant |

The invention claimed is:

1. An agitating device for a digester of a biogas plant having a plurality of agitator blades, each agitator blade comprising a plurality of blade sections angled relative to one another,
    wherein the plurality of blade sections of the agitator blade are each substantially flat and angled relative to one another along separation lines between the plurality of blade sections, and at least a pair of adjacent separation lines extend away from one another with increasing distance from a central rotational axis of the agitating device, such that the agitator blade gradient decreases with increasing distance from the central rotational axis so as to configure the agitator blade with approximately uniform advancing drive over the diameter of the agitator blade,
    wherein pairs of adjacent blade sections define a bending edge disposed in-between and extending substantially linearly, wherein the bending edges show a radial component transverse to a rotational axis, also an axial component parallel to the rotational axis, wherein with the radial distance of a bending edge from the rotational axis increasing, the axial component of the bending edge decreases and wherein the plurality of blade sections comprises at least five consecutive blade sections, wherein the bending lines do not intersect on the surface of the agitator blade.

2. The agitating device according to claim 1, wherein the blade sections are integrally connected with one another and wherein the blade sections are formed by bending over a flat basic body multiple times, the basic body consisting of a metallic sheet material.

3. The agitating device according to claim 1, wherein at least one angle between pairs of adjacent separation lines bending edges is larger than 1.

4. The agitating device according to claim 1, wherein the agitator blades are attached to a blade hub rotatable about a rotational axis wherein each of the agitator blades comprises a blade body and a blade base adjacent to the blade hub.

5. The agitating device according to claim 4, wherein a radially inwardly blade surface extends at an angle between 15° and 75° to the rotational axis of the blade hub.

6. The agitating device according to claim 4, wherein an agitator blade mounted to the blade hub extends in the axial direction of the rotational axis over at least 1/6 of the maximum radial extension of the agitator blade from the rotational axis.

7. The agitating device according to claim 1, wherein at least one of the blade sections shows an elevation transverse to its blade surface that is smaller than four times the material thickness of the blade section.

8. The agitating device according to claim 1, wherein the agitator blade is provided with at least six, eight or more blade sections.

9. The agitating device according to claim 1, wherein at least one blade section is edge-bent.

10. The agitating device according to claim 1, wherein a product of a distance from a central rotational axis and the local agitator blade gradient varies over the blade surface by less than the value of 4 and in particular by less than the value of 2.

11. The agitating device according to claim 1, wherein a local inclination angle in a surface location of the agitator blade relative to an axis extending through the surface location and oriented transverse to the central rotational axis decreases with the distance from the central rotational axis increasing.

12. The agitating device according to claim 1, wherein the agitator blade is attached to a mounting device.

13. The agitating device according to claim 1, wherein a plurality of two, three or more agitator blades is provided.

14. The agitating device according to claim 12, wherein the mounting devices of the agitator blades form a multi-edged axle mount overall.

15. The agitating device according to claim 12, wherein the agitator blade is attached to the mounting device by means of at least one detachable connecting device.

16. The agitating device according to claim 1, having a driving device and at least one drive shaft wherein the agitator blade is at least substantially non-rotatably connected with the drive shaft.

17. An agitating device for a digester of a biogas plant, comprising:
a digester of a biogas plant having a digester wall and at least one digester interior and at least one digester roof and at least one agitating device that is disposed in the digester interior, wherein the agitating device has a plurality of agitator blades, each agitator blade comprising a plurality of blade sections angled relative to one another, wherein the plurality of blade sections of the agitator blade are each substantially flat and bent at an angle relative to one another along separation lines between the plurality of blade sections, wherein the separation lines diverge from each other with increasing distance from a central longitudinal axis, such that the agitator blade gradient decreases with increasing distance from the central rotational axis, wherein pairs of adjacent blade sections define a bending edge disposed in-between and extending substantially linearly, wherein the bending edges show in their orientation other than a radial component transverse to a rotational axis, also an axial component parallel to the rotational axis, wherein with the radial distance of a bending edge from the rotational axis increasing, the axial component of the bending edge decreases and wherein the plurality of blade sections comprises at least five consecutive blade sections, and wherein the bending lines do not intersect on the surface of the agitator blade.

18. A method for manufacturing an agitating device for a digester of a biogas plant having a plurality of agitator blades, each of the agitator blades comprising a plurality of blade sections angled relative to one another,
wherein at least five consecutive blade sections of the agitator blades are each substantially flat and bent over at an angle relative to one another along separation lines between the five consecutive blade sections, wherein the separation lines diverge from each other with increasing distance from a central longitudinal axis, such that the agitator blade gradient decreases with increasing distance from a central rotational axis, and
wherein pairs of adjacent blade sections define a bending edge disposed in-between and extending substantially linearly, wherein the bending edges show a radial component transverse to a rotational axis, also an axial component parallel to the rotational axis, wherein with the radial distance of a bending edge from the rotational axis increasing, the axial component of the bending edge decreases, and wherein the bending lines do not intersect on the surface of the agitator blade.

19. The method according to claim 18, wherein the agitator blade is manufactured from a two-dimensional basic body by bending over each of the blade sections.

20. The method according to claim 19, wherein the two-dimensional basic body is bent over and in particular edge-bent on a separation line between two blade sections.

21. The method according to claim 19, wherein multiple agitator blades are interconnected directly or indirectly via detachable connecting devices.

22. The method according to claim 19, wherein an angle between pairs of blade sections depends on the distance from a rotational axis.

* * * * *